US009423341B1

(12) United States Patent
Jim et al.

(10) Patent No.: US 9,423,341 B1
(45) Date of Patent: Aug. 23, 2016

(54) DAYTIME INFRARED IMAGING OF SATELLITES

(75) Inventors: Kevin T. C. Jim, Honolulu, HI (US); Basil Scott, Waimea, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 988 days.

(21) Appl. No.: 12/956,968

(22) Filed: Nov. 30, 2010

Related U.S. Application Data

(60) Provisional application No. 61/283,155, filed on Nov. 30, 2009.

(51) Int. Cl.
*G01N 21/359* (2014.01)

(52) U.S. Cl.
CPC .................. *G01N 21/359* (2013.01)

(58) Field of Classification Search
CPC ................. G01N 21/359; G01N 2015/084
USPC .................. 250/339.11, 338.1, 340
See application file for complete search history.

(56) References Cited

U.S. PATENT DOCUMENTS

| | | | | |
|---|---|---|---|---|
| 4,598,981 | A * | 7/1986 | Hallam et al. | 359/366 |
| 7,035,375 | B2 * | 4/2006 | Yokhin | 378/86 |
| 7,130,051 | B2 * | 10/2006 | Oppenheimer et al. | 356/445 |
| 7,319,556 | B1 * | 1/2008 | Ackermann et al. | 359/366 |
| 7,349,804 | B2 * | 3/2008 | Belenkii et al. | 701/500 |
| 8,511,614 | B2 * | 8/2013 | Robinson | 244/158.4 |
| 2004/0156087 | A1 * | 8/2004 | Oppenheimer et al. | 359/244 |
| 2007/0125910 | A1 * | 6/2007 | Cepollina et al. | 244/172.6 |
| 2007/0138344 | A1 * | 6/2007 | Cepollina et al. | 244/172.5 |
| 2008/0080078 | A1 * | 4/2008 | Lau et al. | 359/885 |
| 2008/0095303 | A1 * | 4/2008 | Grass et al. | 378/5 |
| 2008/0259447 | A1 * | 10/2008 | Oppenheimer | 359/399 |
| 2009/0009897 | A1 * | 1/2009 | Holota et al. | 359/859 |
| 2009/0051772 | A1 * | 2/2009 | Rhoads | 348/187 |
| 2010/0008558 | A1 * | 1/2010 | Baeumer et al. | 382/131 |

OTHER PUBLICATIONS

Marois, High Resolution Imaging of Satellites with Ground-Based 10-m Astronomical Telescoptes, Feb. 2, 2007, Lawrence Livermore National Lab., pp. 1-19.*
Lambour et al., i.e., Small Aperture Telescope Augmentation Study, Russian Academy of Sciences Central Astronomical Observatory at Pulkovo, Sixth US/Russian Space Surveillance Workshop, St. Petersburg, Aug. 2005.*
Wilson et al. A Wide-Field Infrared Camera for the Palomar 200-inch Telescope, Proceeding of SPIE vol. 4841, 2003.*

(Continued)

*Primary Examiner* — Djura Malevic
(74) *Attorney, Agent, or Firm* — James Creighton Wray; Meera P. Narasimhan

(57) ABSTRACT

GEO satellites and other space objects are studied in daylight, twilight and at night using IR cameras in clusters of no more than three with programs for pointing the instruments at known locations of the GEO objects and satellites and receiving weak near IR signals. Detection instruments have minimal optical surfaces and simple optical paths directing IR through Kshort and combined Kshort and H near IR band filters in cryogenic assemblies. Large focal ratios and large apertures reduce the effect of sky brightness, lower noise and improve the target signal, increasing the noise to signal ratio. Sky background noise is reduced by co-adding hundreds of pixels, allowing for the faint IR signal integration of one second or more. Results are read after integration.

23 Claims, 8 Drawing Sheets

(56) References Cited

OTHER PUBLICATIONS

Proceedings of the 19999 Space Control Conference, Lincoln Lab MIT, Apr. 13-15, 1999.*
Dunham et al. PSST: The Planet Search Survey Telescope, Publications of the Astronomical Society of the Pacific, 116:1072-1080, Nov. 2004.*
Christopher et al. A catalogue of potential adaptive optics survey fields from the UKIRT archive Mon. Not. R. Astron. Soc. 365, 439-446 (2006).*
Chakraborty et al., The Nature of Faint Companions to G-Type Stars From Adaptive Optics, The Astronomical Journal, 124:1127-1131, Aug. 2002.*
Vaduvescu et al., Strategies for Imaging Faint Extended Sources in the Near-Infrared, Publications of the Astronomical Society of the Pacific, 116:640-651, Jul. 2004.*
Cooray et a., Cosmic Infrared Background ExpeRiment (CIBER): A Probe of Extragalactic Background Light from Reionization, http://arxiv.org/abs/0904.2016v1.*
Rork et al., Ground-Based Electro-Optical Detection of Artificial Satellites in Daylight from Reflected Sunlight, Lincoln Laboratory project Report ETS-63 May 25, 1982.*
Pickering, The MMT All-Sky Camera, Proc. SPIE 6267, Ground-based and Airborne Telescopes, 62671A (Jun. 23, 2006); doi:10.1117/12.672508.*
Stobie et al., Data Mining the MMT All-Sky Camera, Astronomical Data Analysis Software and Systems XVII P3.9 ASP Conference Series, vol. 394, c 2008.*

* cited by examiner

FIG. 3
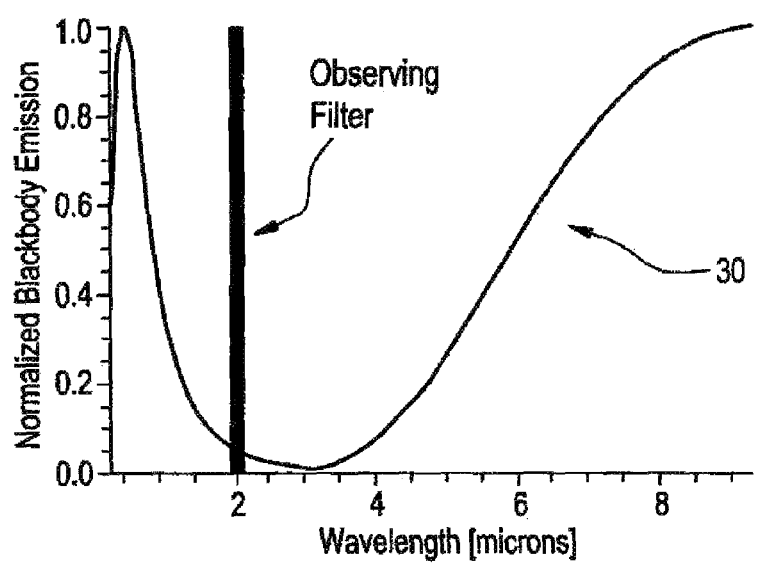
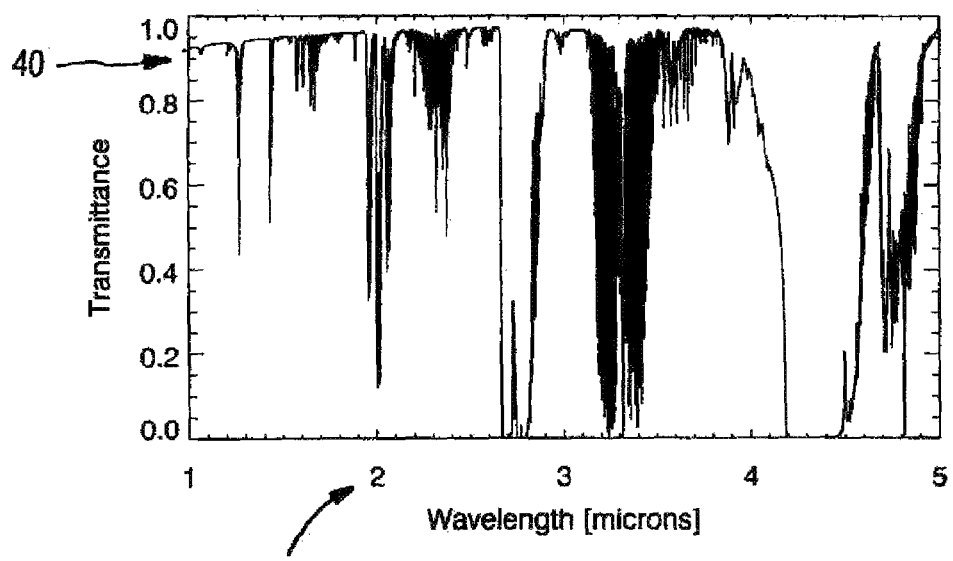
FIG. 4

DAYTIME INFRARED IMAGING OF SATELLITES

This application claims the benefit of U.S. Provisional Application No. 61/283,155, filed Nov. 30, 2009, which is hereby incorporated by reference in its entirety as if fully set forth herein.

This invention was made with Government support under Contract [No.] awarded by [the Department of the Navy]. The Government has certain rights in this invention.

BACKGROUND OF THE INVENTION

Optical capabilities for space situational awareness (SSA), and in particular for the geosynchronous Earth orbit (GEO) regime are highly desired as an augmentation of current radars. In a general sense, optical telescopes are better suited than radar systems to GEO observations due to problems of reduction in detection of reflected flux. In addition, bright daylight skies make observing dim objects challenging, because of increased system noise, camera saturation and short exposure time.

Optical telescopes in the Space Surveillance Network (SSN) used to monitor the GEO satellites operate only at night. Depending upon the sensor location, night time observations might be possible for 10 to 14 hours per 24-hour day, leaving a gap in observation capability from 10 to 14 hours per day. Daytime observations are quite important, but currently are handled mostly by a few radar systems. Current radars do not provide full global coverage and thus cannot detect many GEO objects. In addition, radar sites are expensive to operate and maintain. The radars must overcome the fact that they transmit power in a beam that must be reflected and detected upon reflection. A decrease in efficacy is proportional to the beam fading in power over twice the distance between the radar and the satellite. That is referred to as the $1/r^4$ problem. Optical systems experience a reduction in the detection of flux reflected from the satellite proportional to $1/r^2$.

At 36,000 km altitude above the Earth, GEO satellites are much farther away than low earth orbit (LEO) satellites, which are often found at altitudes between 300 and 1000 km. Since the GEO satellites are approximately 100 times farther than LEOs, GEOs will be 10,000 times fainter, all else being equal. An $8^{th}$ magnitude LEO object at 360 km if placed in a GEO*/orbit would become $18^{th}$ magnitude object.

In addition, the bright daylight skies make observing dim objects challenging because of increased system noise, camera saturation and short exposure times. For a sky brightness increase of 100 to 500 times, which is typical of IR observing bands in the day, noise will increase by approximately the square root, or 10 times to 25 times. This reduces system detection capability by ~3 to 5 magnitudes. At night, exposure times of minutes are used to see very dim objects, but in the day, maximum exposure times may be less than 1 second before the camera signal is saturated to a maximum level.

GEO satellites are expensive and tend to be quite large, which makes them brighter than smaller LEO objects, thus brighter than $18^{th}$ magnitude. They typically have large, steerable solar arrays, which have areas in the tens of square meters. The faces enlarged somewhat mitigate the issues of distance and daylight viewing.

In FIG. 1, the results of the European Space Agency's 2006 survey of the GEO belt are shown (from R. Jehn, H. Klinkrad, H. Krag, T. Flohrer, and R. Choc. ESAs Optical Ground Station at Tenerife. OPS-G Forum, 18 Jan. 2009, 2008). This data shows that there is a nominal distribution of brightnesses at night, which can be translated to daytime magnitudes as described in the following section. It can be seen that, if the limiting magnitude of a system is equivalent to the translated visual magnitudes in the daytime geometry and wavelength of observations is equivalent to $14^{th}$ to $15^{th}$ magnitude, a significant fraction of the population can be followed.

SUMMARY OF THE INVENTION

The present invention provides imaging of satellites and other space objects and tracking of satellites from the Earth. The invention provides cameras and telescopes that suppress through the use of cold traps infrared background from telescopes and optics, as seen by the infrared detectors. Interactive background subtraction combined with shifting and adding to remove background noise improves the signal to noise ratio.

The invention addresses the problems unique to satellite imaging [and other faint space objects], including stacking and combinations of frames as stars move through the field.

The system would be valuable to satellite operators and others interested in SSA, who would like relevant space information during the daytime.

This invention explicitly suppresses the background infrared contribution from telescope and camera optics. In addition, the new invention uses a shift and stare technique, combined with interactive background subtraction. In this new technique, the contributions from stars are removed in addition to the contributions from the background. The background subtraction occurs on a per-pixel basis, as well.

The new infrared (IR) capability will allow a system to achieve operations continuously, day and night, provided that clouds of too great of an optical thickness do not intervene. The invention provides an infrared capability in persistent observational surveillance for enhanced space situational awareness. This invention addresses the gaps by extending IR sensor technology to achieve a capability that is over 100× more sensitive than currently-fielded systems, such as the Daylight Acquisition System (DAS).

The geosynchronous orbit (GEO) belt is of strategic importance to the U.S. because of the large number of vital communications and Earth-observation satellites in GEO. At 36,000 km above the Earth's equator, the orbital velocity of satellites in circular orbits matches the speed of the rotation of the Earth. Within the GEO regime, there are geostationary satellites, which maintain their position over a location on the Earth, other satellites with orbits that incline to the equator, as well as other satellites that do not actively maintain their position or are in slightly different orbits, such as disposal orbits, and thus move slowly relative to the Earth's surface. GEO objects are subject to perturbations caused by the gravity of the Sun and the Moon, variations in the distribution of the Earth's mass, solar radiation pressure, and other small effects that cause satellites to drift from stationary positions. Monitoring of the satellites in the GEO belt is necessary to maintain knowledge of their orbits to avoid collisions, to understand whether the satellites are maintained under operator control or, if they are out of control, to help to determine why a satellite that fails might have failed, and to determine what is wrong with satellites that are having control problems, in order to regain proper operations, and potentially to detect attacks upon GEO satellites belonging to the U.S. or our allies. Providing persistent space situational awareness for the GEO belt is a high priority for USSTRATCOM as well as USPACOM.

Persistent surveillance requires full 24/7 coverage of the entire belt, including day and night observations.

The technology also addresses the issues posed by the spatial-temporal sky variation, and thus realizes the significant benefits possible through frame co-adding and gives equivalent integration times of many minutes, which is appropriate for GEO objects.

The technology would work well within a ground-based intelligent network of autonomous small (~0.5 m+) telescopes. The complete network system could include multiple sites with multiple sensors at each site distributed globally. Site specific manning could be as few as 2 mandays per months per site, as an example.

The system provides continues, 24 hours per day, 7 days per week, day and night coverage for GEO observations including metrics and characterizations for catalog updates, persistent custody, and change detection. The new system brings new and complementary capabilities to space situational awareness (SSA) and does not duplicate existing or future planned systems. The new system provides information, precision, quality, security, timeliness and sharing of information and reach, persistence, agility and a broad spectrum of operations.

Existing SSA sensors include radar and optical systems. A current optical system used for space object catalog maintenance is the Ground-Based Electro-Optical Deep Space Surveillance (GEODSS), which has three sites, each with three 1–m telescopes, and one site with a single telescope. Site-specific manning is ~600 man-days per months per site. Site cost is ~$25 M. GEODSS operates only at night. GEODSS does not provide daytime coverage, and is unable to provide real-time data on events, such as satellite launches or maneuvers.

The new system differs from GEODSS in the context of space awareness attributes in several ways. The new automated processing improves the timeliness of information of SSA, providing timely data, change detection, maneuver detection and more. This results from the combination of frequent, hourly observations of objects, automated processing, and succinct, automated reporting. Its control center is capable of producing intermediate-level and high-level data products, improving the precision of information. While current sensors act as data collectors, the new system paradigm includes mission processing, orbital determination, conjunction analysis, cross-tagging, and other capabilities included in the baseline and a continuously growing set of products distributed to the SSA and space control communities via the netcentric paradigm.

The new sensors can be integrated with and can be tasked by existing command and control. In addition, all information and data products generated by the new network will be made available to the community of users through a gateway at the system control center, improving the sharing of information.

The technology and a network would improve the reach of operations of ground-based SSA, including unmet geographic coverage. Additionally, the new infrared daylight capability extends the reach of ground-based optical observations into the daytime. New rapidly deployable mobile sensors can extend reach on demand. For example, sensors could be position in areas better able to characterize threats from orbital debris, should the orbital geometry of the debris be difficult to observe with existing assets.

The new system can immediately provide extended persistence of operations not available from GEODSS through a multitude of methods. The geographically distributed sensors provide persistence to weather outages that GEODSS currently cannot. The ability to extend night time operations into twilight extends persistence of visible sensors. The infrared daylight capability provides daytime persistence of operations.

The new network provides agility of operations not available with GEODSS. The new system incorporates intelligent network tasking that is interruptible and rapidly re-taskable. This supplies the flexibility required to ensure support for high-priority, time-sensitive, and urgent requests for information. Data products are transmitted to the requester within minutes of completing the collection and data reduction. In addition, the new architecture incorporates a network centric control ability, continuously optimizing tasking across all sensors in the network and ensuring success for high-priority missions. These capabilities mitigate single-site outages from weather, site maintenance, etc, and ensure missions are accomplished.

The new system improves the spectrum of operations of SSA, including GEODSS, providing characterization data including photometric and multi-spectral data. This allows for space object identification (SOI) to reduce cross-tagging of objects. Additionally, simultaneous collections by multiple sensors provide attitude recovery data for determining where a satellite may be looking. Future planned systems include a space based space surveillance (SBSS).

The space surveillance telescope (SST) will be 3.5-meter f/1 telescope with a large, curved focal plan array. Projected cost for the first telescope to be installed in New Mexico is $65 M. The space surveillance telescope (SST) program develops technology for the curved focal plan array sensors to enable innovative telescopes that combine high detection sensitivity, short focal length, wide field of view, and rapid step-and-settle to provide orders of magnitude improvements in space surveillance. The goal for the SST is a set of 5 of these advanced large telescopes in place by 2020.

The present invention improves SST performance and addresses some shortfalls.

The new invention is a gap-filler that is operable seven years in advance of the planned SST. The invention provides weather mitigation. Weather causes outages at all sites. A widely-distributed new network provides supporting partial back-up coverage in a cost-effective package.

The invention provides follow-on and hands-off tasking. When SST observations indicate that there is an object of interest, the SST system could pass that item to a network of the present invention for follow-on observations, allowing the SST telescope to return to its primary mission of synoptic search.

The invention provides contingency and recovery operations. If an SST site is down for any reason, the present new network sites with overlapping fields of regard provide coverage, preventing a mission-critical outage in space situation awareness. Rapidly deployable new system sites can be fielded to add capacity or to provide partial back-up service any time a site is down.

Relative to total space awareness the new invention is differentiated from SST. The new system provides timeliness of information. A new system gap-filler could be in use in 2011, and fully constructed in 2012, seven years in advance of the planned completed site SST system.

The new system provides expanded reach of operation. The ability of the new system extends night time operations into twilight, which extends reach of visible sensors. The infrared daylight capability provides daytime reach of operations.

The new system employs 9 sites and 27 sensors for a fraction of the cost of any other SSA asset. This geographic distribution and autonomous network sensor re-scheduling enables persistence of operations through weather and other planned or unplanned sensor outages.

The SST requires specially developed curved focal plan arrays, limiting the ability to change operations due to the lack of commercially available technology that can support the SST. The new system exploits the most advanced CTS technology, can be rapidly upgraded to support enhanced operations and can provide agility of operations unavailable from SST. Unlike the orbiting SBSS, sensors of the new system can be repaired and replaced inexpensively.

The new system provides the range of the spectrum of operations for SSA including SST by providing characterization data including photometric, multi-spectral data. This allows for space object identification (SOI) to reduce cross tagging of objects. Additionally, simultaneous imaging by multiple, distributed sensors improves the determination of satellite attitude.

The space based space surveillance (SBSS) system will be a visible-wavelength wide-field-of-view optical sensing satellite at an altitude of 800 kilometers in a near-polar sun-synchronous orbit. First launch is now planned for July 2009. Cost for the first satellite in the system is given by the Air Force as $823.9 M including ground based infrastructure. The nominal goal is for a constellation of 4 satellites by 2013. The initial satellite is expected to last about five years on orbit.

Relative to space awareness, the new system is differentiated from SBSS.

The new system provides timeliness of information and, as a gap-filler will be on line for 1-2% of the cost of SBSS. The first satellite for SBSS is planned for launch in July 2009 with potential future systems in discussion.

The new system provides resilience of operation. The new sensors are easier and less expensive to repair and maintain than a spaced-based asset. In an operational configuration, even a fully redundant and hardened system is orders of magnitude less expensive than a space-based system. Geographically dispersed ground stations are faster to deploy, cheaper to install, and easier to upgrade and maintain than a spaced-based system.

The new system provides agility of operations. The new ground-based asset can be upgraded to the latest technologies and methodologies at minimal cost. The new architecture continuously leverages advances in technology, whether developed by the government or industry.

The new system provides spectrum of operations and augments and improves the range of the spectrum of SSA operations supported by existing and planned SBSS, SST, etc. by providing ground-based agile, timely, persisting, globally reaching operations for GEO surveillance.

The invention fills current capability gaps now, at a very low cost, and provides data assurance for future systems, if and when they are deployed.

New automated ground stations require very little supporting infrastructure either in facilities or staffing and can adopt and prototype new technology quickly in the new network then lever them into other systems when they are mature.

The new system incorporates a data processing and data reduction control center. The system is offering more than just more metric and SOI collects. One of the plaguing issues today is that more data can be generated than can be converted into useful data products. The new network can generate intermediate and high-level data products in addition to providing a tremendous increase in capacity for metric and SOI collections.

The new invention incorporates into existing SSN command and control as well as into the extended space systems architecture SSA. The new system is usable immediately under existing conditions and doctrine. The data is available to the entire community via ESSA, and the architecture is designed from the ground up to be able to support the evolving net-centric systems.

These capabilities make an excellent adjust to existing acquisitions. It is possible to prototype hardware, software and systems that can later be leveraged into space-based systems (SBSS) or more expensive ground-based systems (SST). In addition, the new system has rapidly deployable mobile components. That makes it useful to cover for an existing sensor optical or radar and pick up part of their mission load if they are down for maintenance, or for any unplanned reason.

Faint near IR reflections from geosynchronous satellites, objects and photovoltaic arrays are detected in instruments with advanced detectors having low read noise and small pixels, simple light paths and small numbers of optical surfaces. The dedicated optical instruments have large focal ratios and large COTS apertures. The detecting of the IR reflections occurs during daytime, twilight and night. The large focal ratios reduce effect of sky brightness and lowering noise. The larger apertures improve target signal and increase signal to noise ratio.

Instrument clusters have no more than three lenses, dewar windows and filters. The instruments are IR cameras with serviceable dewar windows and full control chip setup software.

The faint near IR reflections are integrated through long integration times as information and then read.

The near IR cameras have detector chips that are removable and exchangeable. Cryogenic assemblies have changeable cold stops and near IR band filters in the cameras. Filters designed for improved signal-to-noise ratios (SNRs) for imaging through the atmosphere are used in the near IR cameras. These include the J, H, Kshort, K, and potentially L filters. Combined Kshort and H near IR band filters are also used for daylight sensing. Filters specifically designed for particular site conditions are also used.

Reduced sky background is detected between a scattered sunlight region longer than 1 µm and shorter in wavelength than the thermal region which has wavelengths longer than 3 µm. InSb and HgCdTe detectors fully detect this range of wavelengths, from 1 to 3 microns.

Near IR cameras with cryogenic assemblies have IR band filters as described above in the cryogenic assemblies. The effects of the very bright background are removed by frame co-adding of hundreds of image frames and iteratively removing the background. This allows integration times of 1 second and obtains performance levels in detecting GEO satellites of more than $14^{th}$ magnitude. 300 or more small pixels are used as the image frames. In one implementation, the pixel size is 20 microns square.

Conditions of GEO satellites and objects are obtained by dispersing the described systems around the world in GEO satellite positioning regions and directing the telescope and camera systems at known satellites and reporting status of the satellites.

A system has an instrument for faint IR detection from a geosynchronous object (GEO). The instrument is pointed at a known location of a GEO. The instrument has a large f-number (F#), a large aperture (which may be commercial, off-the shelf), a cryogenic assembly with changeable cold stop and near infrared filters (J, H, Kshort, K, L, and custom filters) and an advanced detector with low read noise and small pixels. Co-adding images from the hundreds of pixels reduces background noise and allows integration for one second or more.

These and further and other objects and features of the invention are apparent in the disclosure, which includes the above and ongoing written specification, with the claims and the drawings.

BRIEF DESCRIPTION OF THE DRAWINGS

FIG. 3 is a model of the atmosphere using the industry-standard MODTRAN code for the daytime at 8 AM from a high-altitude site. The scattered light from the sun dominates the shorter wavelengths in this plot, and the thermal emission increases in the longer wavelengths of this plot. There is a minimum between the two functions in the near infrared.

FIG. 4 shows the transmittance of the atmosphere in the near infrared during the daytime, as modeled by MOD-TRAN for Mauna Kea Hi.

DETAILED DESCRIPTION OF THE DRAWINGS

Figure 1:
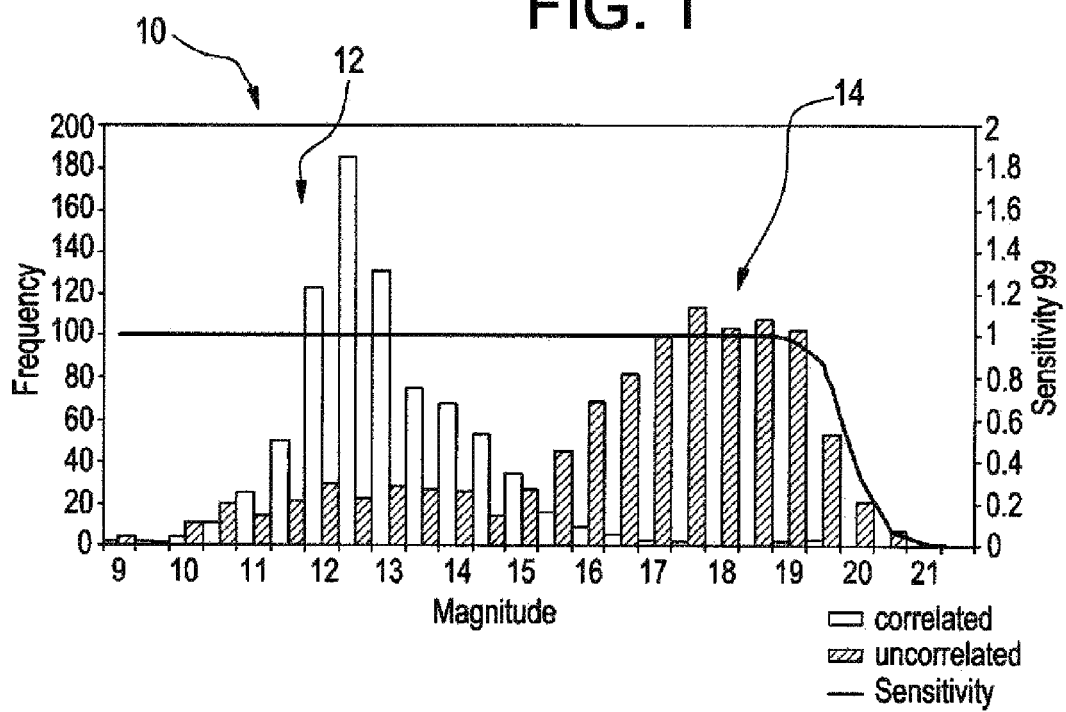
FIG. 1 shows the GEO/GTO (geosynchronous transfer orbit) belt population in 2006 as surveyed by the European Space Agency.

FIG. 1 shows a chart 10 of the GEO/GTO (geosynchronous transfer orbit) belt population in 2006 as surveyed by the European Space Agency. Correlated 12 objects are those listed in the U.S. Space Surveillance Network's publicly available catalog, and uncorrelated objects 14 are not listed in the catalog.

The instrument used with the invention is a dedicated system for IR faint GEO object detection rather than used as a multi-use or fast tracking sensor. Specifically, this means using an appropriately large F#, or focal ratio, a larger COTS aperture that is available and that can work within the physical constraints of other system components, and an advanced detector with low read noise and smaller pixels. Also, light paths are kept as simple as possible with the smallest number of optical surfaces.

Table 1 shows the performance results that can be achieved by modifying four specific areas with respect to current designs. Larger F#'s reduce the effect of sky brightness, and thus lower the noise. Larger apertures improve the target signal, thus increasing the signal to noise ratio signal to noise ratio (SNR). High performance cameras reduce camera read noise, and their smaller pixels modestly reduce noise from sky brightness.

The invention employs less optical surfaces than systems which are multi-use/multi-mission instruments. The new instrument cluster uses no more than three lenses, plus a dewar window and filters. Current systems use nine to fourteen lenses and tertiary mirrors. The extra complexity in the current systems is necessary because of their multi-use role; also, those instruments have relatively large field-of-view and small F#, which is required due to their mission role.

The new dedicated system has the effect of moving system performance from magnitude 7/8 to an improved performance of magnitude ~10.

Applying technology developed under Oceanit's missile defense program to the GEO SSA problem provides improved performance and greater system flexibility. Oceanit has integrated IR systems with custom and commercially available IR sensors. These activities have included systems that operate at sea level, Makaha Ridge 1700 feet, and on air platforms at 40,000 feet.

A new configurable camera system is used with serviceable dewar and full control chip setup software. The camera system, from SEIR, is the de facto standard in the IR missile defense community for astronomical sensing and is commonly used for many test and experimental astronomy systems. The system allows flexible operation of cameras. Operation of the camera in Aintegrate then read@ mode instead of the typical Aintegrate while read@ mode allows longer integration times, which are appropriate for K band daytime observing. The best available detectors are used in the flexible camera system that allows detector chips to be changed out. Test, mid-performance, and high-performance configurations are available at different cost points.

Figure 2:
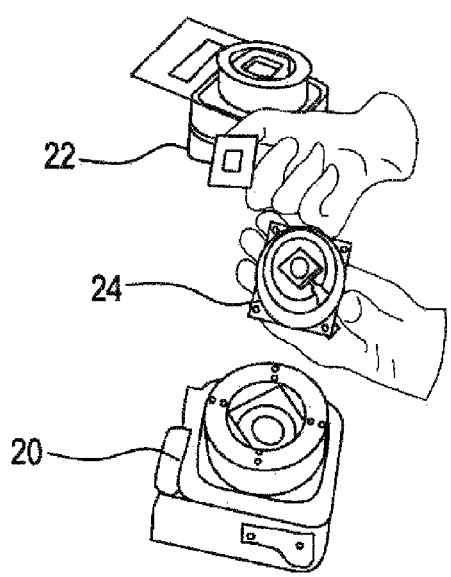
FIG. 2 shows an Oceanit technician changing FPA, cold stop and filter in a cryogenic assembly.

FIG. 2 shows a technician changing a Kshort band filter 22 and cold stop 24 in a cryogenic assembly 20.

Use of optimized filters and sensing bands; for example, Kshort filters (1.00 to 2.31Φm) are used for daylight sensing, as well as a dual band filter for a special sensing application. The Kshort band sensing filters produces superior ground-based results. Analysis shows that Kshort or a combined Kshort and H band are likely to provide a significant advantage for daytime missions. The Kshort senses in the reduced sky background between the scattered sunlight region (below 2 Φm) and the thermal region (above 2.5 Φm). The SEIR camera system allows the camera to be customized with these filters, which are inside the cryogenic chamber.

FIG. 3 shows the simplified blackbody emission 30 of the sun and the atmosphere modeled as a ~300K blackbody. There is a minimum between the two functions in the near infrared.

InSb and MCT detectors made from these materials are lower noise and offer more flexible choices for the spectral observing band than InGaAs cameras. InGaAs supports partial H only, whereas InSb and MCT support full H and K.

Table 2 shows a comparison of system performance. Together these technologies, as shown in Tables 1 and 2 provide a 2-3 magnitude performance increase, resulting in a total improvement (items 1 through 6) of ~5 magnitudes or better. This brings the system performance into the $12^{th}$ magnitude range or better.

Background mitigation and long integration times are provided. In addition to an optimized system and technology insertion improvements, the system incorporates sophisticated background mitigation techniques that are currently used on the largest telescopes in the world. These techniques enable longer integration and/or more extensive image frame co-adding than would otherwise be possible. Applying the sophisticated background mitigation, which was developed for nighttime IR observing, requires a multi-point dither or nodding observation pattern that is matched to the post-processing algorithms that are applied.

Table 3 shows continued comparison of system performance with frame co-adding without background mitigation produces improvement factors of ~5×, which are consistent co-adding results.

Summarizing all of the improvements from best practice IR design, lessons-learned, and research to integrate high performance background mitigation, the total improvement is 8+ magnitudes. This results in a performance level of better than 14$^{th}$ magnitude, which meets an objective performance goal.

Table 4 compares a prototype system, Mojave and final target systems.

Two aspects involve specific innovations. These are: use of Kshort and/or combined Kshort plus H band filters, and use of sophisticated background mitigation in combination with co-adding of hundreds of image frames.

The choice of an optimal filter is complex and offers the opportunity of significantly improved performance. As indicated in tables 2 and 4 above the improvement is a factor of 3×. GEO objects are modeled as diffuse, reflective spheres, with an albedo of 0.2, and with a sun-object-observer angle (phase angle) of 60 degrees. A mean value of the solar illumination is reflected off of the object and is propagated through the atmosphere to the observer. By performing MODTRAN simulations, the absorption of the atmosphere can be modeled reasonably well, and thus the magnitude of the object can be estimated. FIG. 2 shows the results of a MODTRAN simulation for Mauna Kea, Hi.

FIG. 4 shows the transmittance 40 of the atmosphere in the near infrared wavelengths 42 in micros 44, as modeled by MODTRAN for Mauna Kea, Hi.

Using this transmittance, combined with the assumptions above, the peak of the GEO distribution is calculated to lie around magnitude 11 in Kshort. In addition, GEO satellites contain large solar cell arrays, which are more reflective in the infrared than in the visible. That is due to the optimization of the anti-reflection coatings on the solar cells to improve their sunlight-to-electricity conversion. In FIG. 3, the reflectivity is more than doubled in the near infrared when compared with the visible. Thus, the expected peak of the GEO distribution could be as bright as 10.3 in Kshort vs. a visible magnitude of 12, as shown in the European Space Agency data from FIG. 1. This equates to a performance improvement of 1.7 magnitudes, or ~5× over visual. The Kshort band is superior to the H band, due to the reflectance notch shown in FIG. 5 between 1.5 and 2 Φm.

Figure 5:
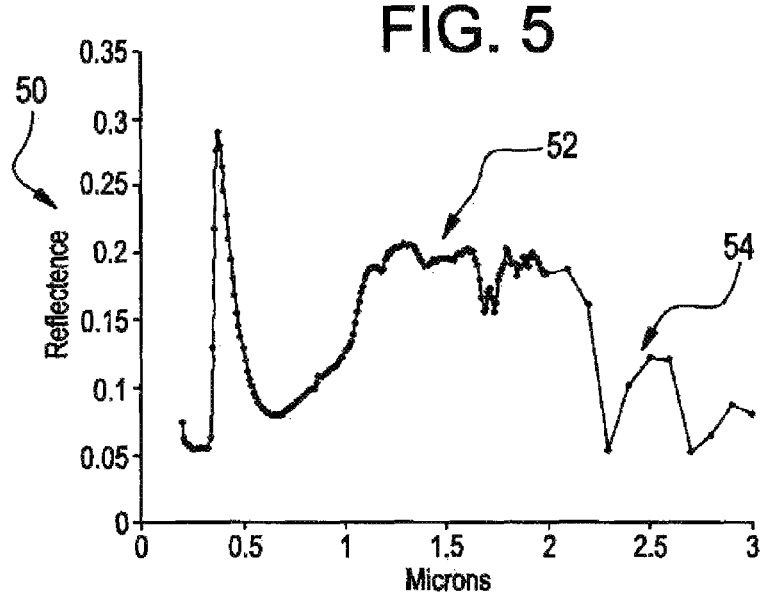
FIG. 5 shows reflectance of satellite solar cell arrays, from the TASAT software (Time-domain Analysis Simulation for Advanced Tracking).

FIG. 5 shows reflectance 50 of satellite solar cell arrays, from the TASAT software (Time-domain Analysis Simulation for Advanced Tracking (Riker, J. F, and Butts, R. R., 1992, Proc. SPIE, A93-37102 14-74, p 548.)) Note that the reflectance is doubled 52 in the near infrared as compared to visible wavelengths 54.

Background mitigation is combined with co-adding. Co-adding frames, as shown in tables 3 and 4 above, can result in significant improvement in system performance. However, co-adding frames is complicated by naturally occurring variations in the sky background. The brightness of the sky, as seen in IR bands, varies in time across the entire field-of-view of a telescope system. The brightness of the sky also varies spatially within the field-of-view.

Figure 6A:
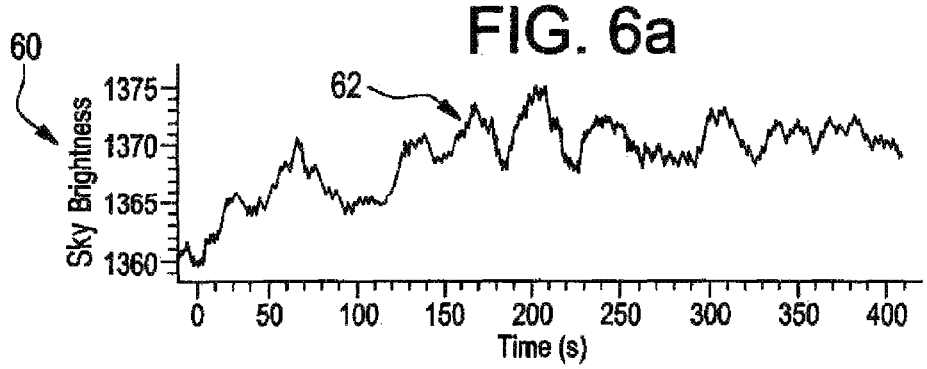
FIG. 6 shows temporal variation of sky background brightness in the IR from mid-infrared sky brightness site testing at the South Pole.
Figure 6B:
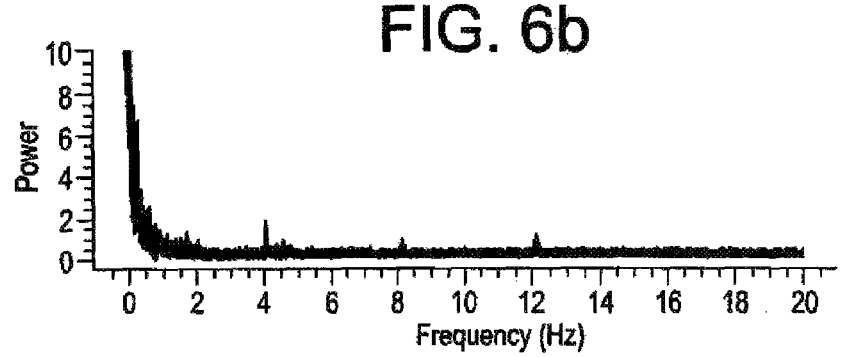

Total IR sky brightness within a telescope field-of-view can change on the order of 1% in one minute, as is shown in FIG. 6. This data was from a mid-latitude site (Canberra) at night. During the day, very clear sites, such as Mauna Kea, may be better, but for typical sites, this data is a low estimate for expected daytime variations, which will be increased due to OH spectral emission.

FIG. 6 shows temporal variations 62 of sky background brightness 60 in the IR from mid-infrared sky brightness site testing at the South Pole, by Smith and Harper, June 1988, Astronomical Society of the Pacific.

Based on the Fourier frequency analysis, this variation begins to create difficulties when co-adding image frames to attain equivalent exposure times longer than 1 to 2 seconds, as well as for camera integration times longer than 1 to 2 seconds. Unless background mitigation techniques are employed, co-adding frames with varying background reduces the signal-to-noise ratio below that which would be achievable against a stable background. Shifting signals result in larger pixel-to-pixel standard deviation within the co-added images than would be the case with a stable background.

Figure 7:
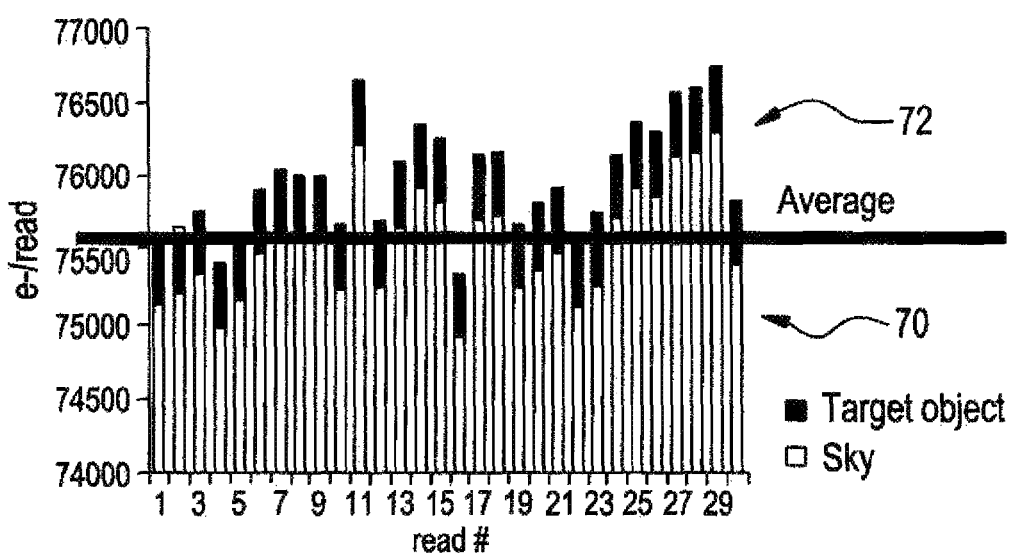
FIG. 7 shows temporal variation of sky background brightness in the IR (mid-infrared sky brightness site testing at the South Pole.

As an example, consider a case in which 30 one-second frames are co-added. FIG. 7 shows the results of a simulation of a case using flux and noise values derived from an IR performance model with a Monte Carlo simulation of the sky variation. The variation depicts what would result with aperture photometry and a 0.5% sky variation, which is statistically similar to the Canberra nighttime data.

FIG. 7 shows the temporal variation of sky background brightness 70 and target object brightness 72 in the IR (Mid-Infrared Sky Brightness Site Testing at the South Pole, Smith and Harper, June 1988, Astronomical Society of the Pacific).

The AAverage@ line indicates the average sky value during this period. When these frames are co-added, about ⅓ of the values are so low that the target makes little or no contribution to the co-added result. The target contribution is reduced to about 2 in a few additional frames as well. This models the case of co-adding without background mitigation, and it is clear that the co-added SNR will be significantly reduced. This simulation considers temporal variation only and not the spatial variation within a frame, which will further degrade the co-added SNR.

Figure 8:
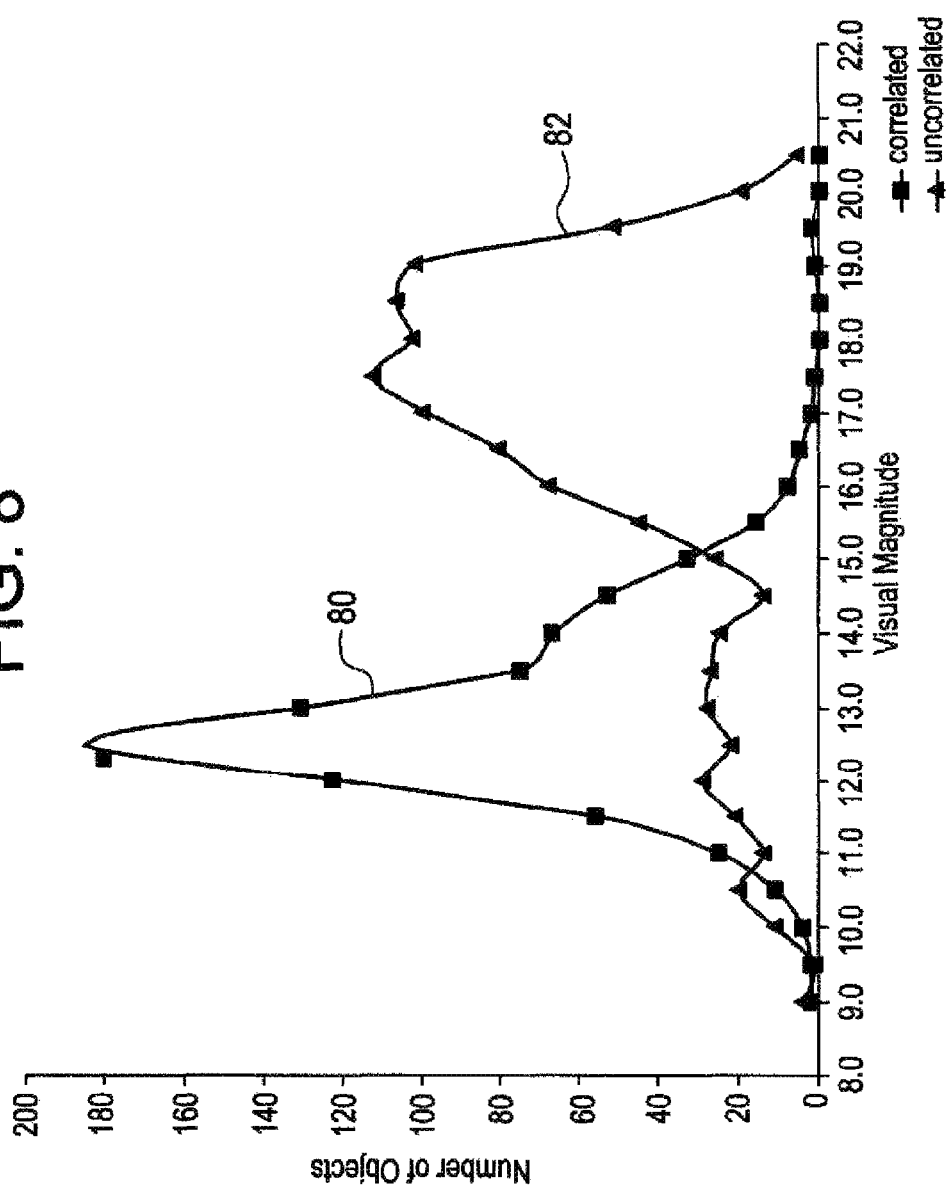
FIG. 8 is a chart comparing correlated and uncorrelated objects at visual magnitudes.

FIG. 8 is a chart comparing correlated and uncorrelated objects at visual magnitudes. The numbers of correlated objects 80 are largest at a visual magnitude of about 12.5. The numbers of uncorrelated objects 82 are greatest between visual magnitudes of about 16.0 and 20.0.

Figure 9:
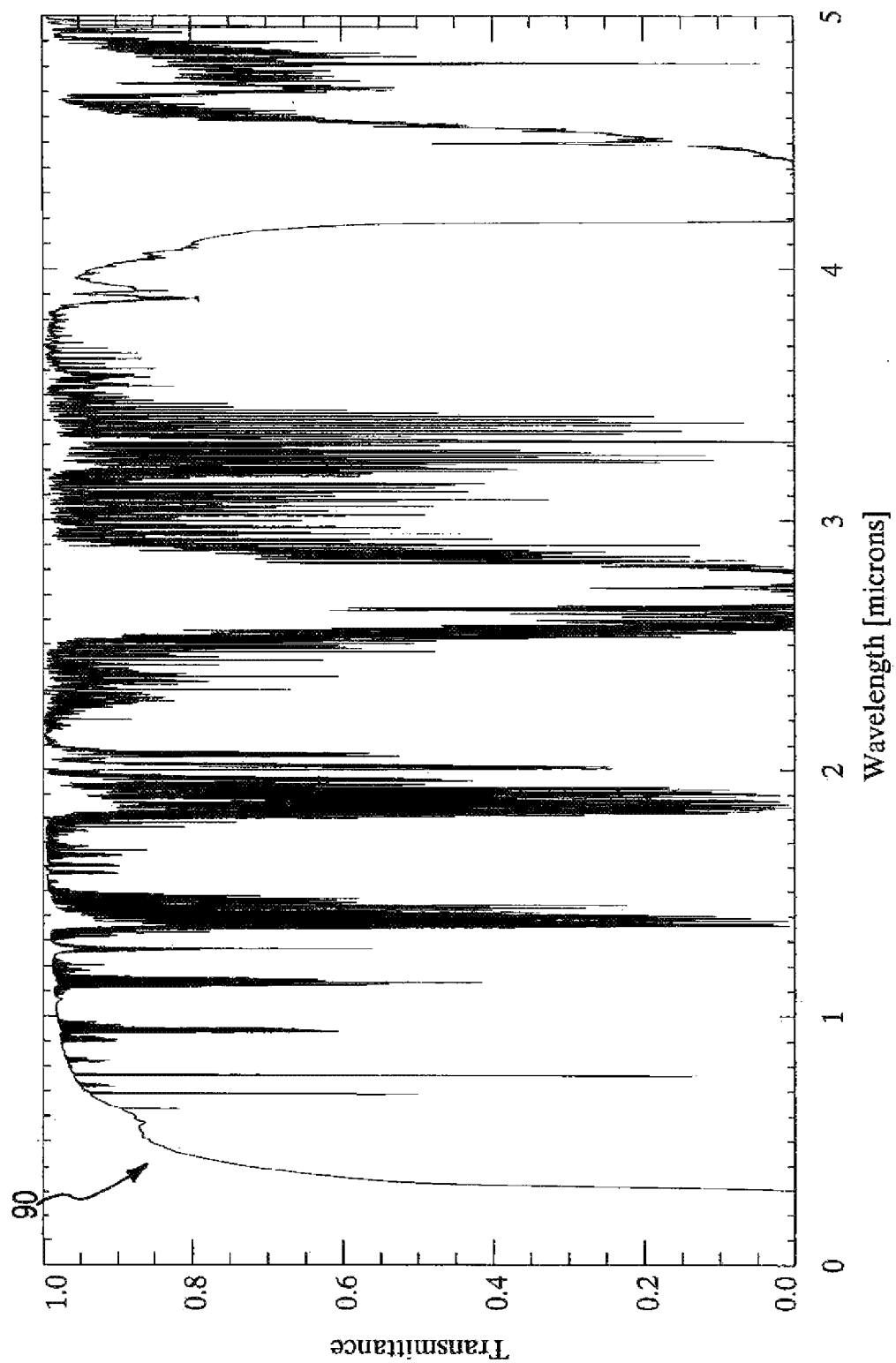
FIG. 9 is a chart comparing transmittance and wavelengths in microns.

FIG. 9 is a chart comparing transmittance and wavelengths in microns. Transmittance 90 is highest between about 0.4 and 2.5 microns and 3.0-4.0 microns and lowest about 2.6-2.8 microns and 4.2-4.5 microns.

Figure 10:
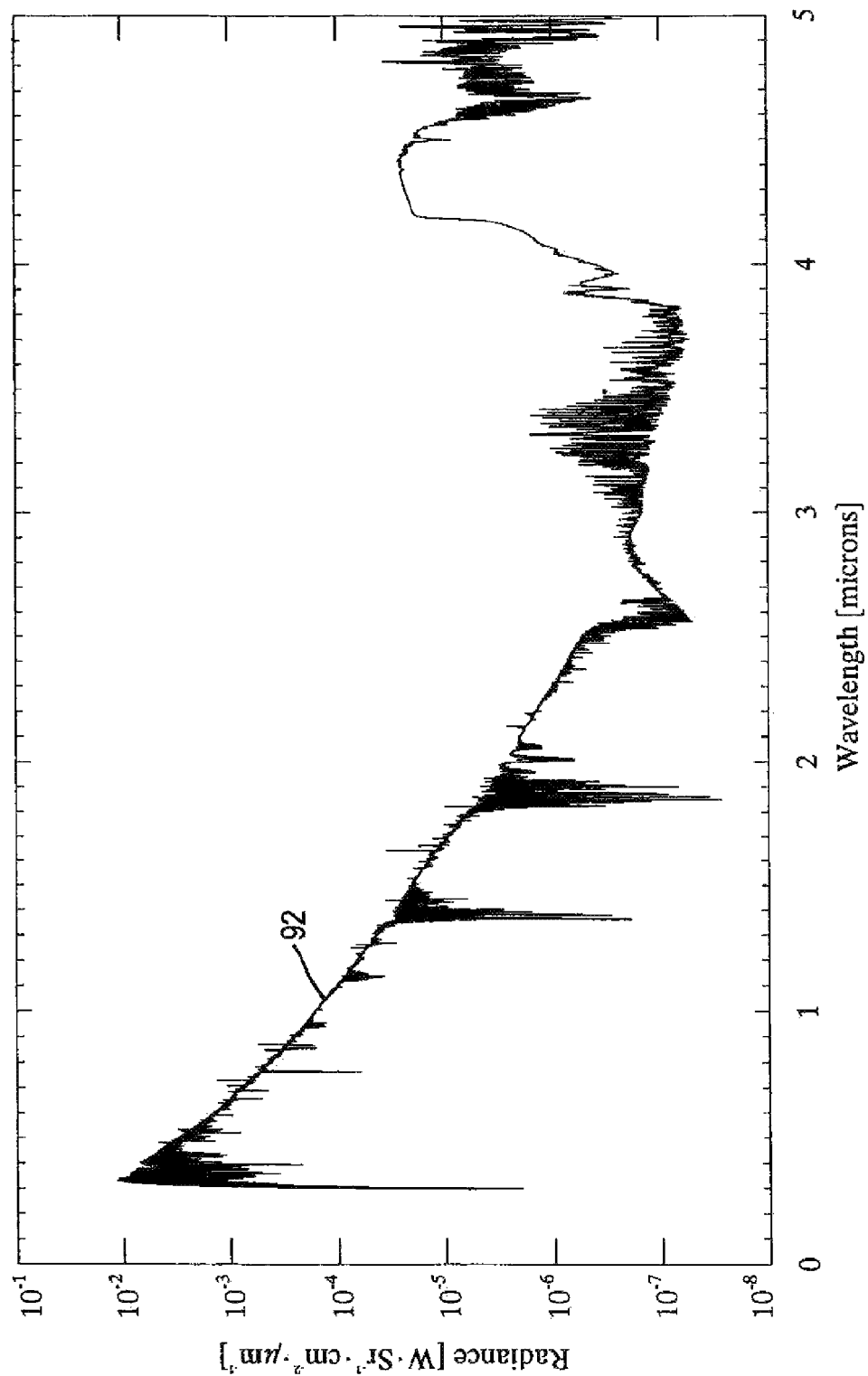
FIG. 10 is a chart comparing radiance and wavelengths in microns.

FIG. 10 is a chart comparing radiance and wavelengths in microns. Radiance 92 is highest in wavelengths of about 0.3 microns and lowest at wavelengths between about 2.5 and 4.0 microns.

Figure 11:
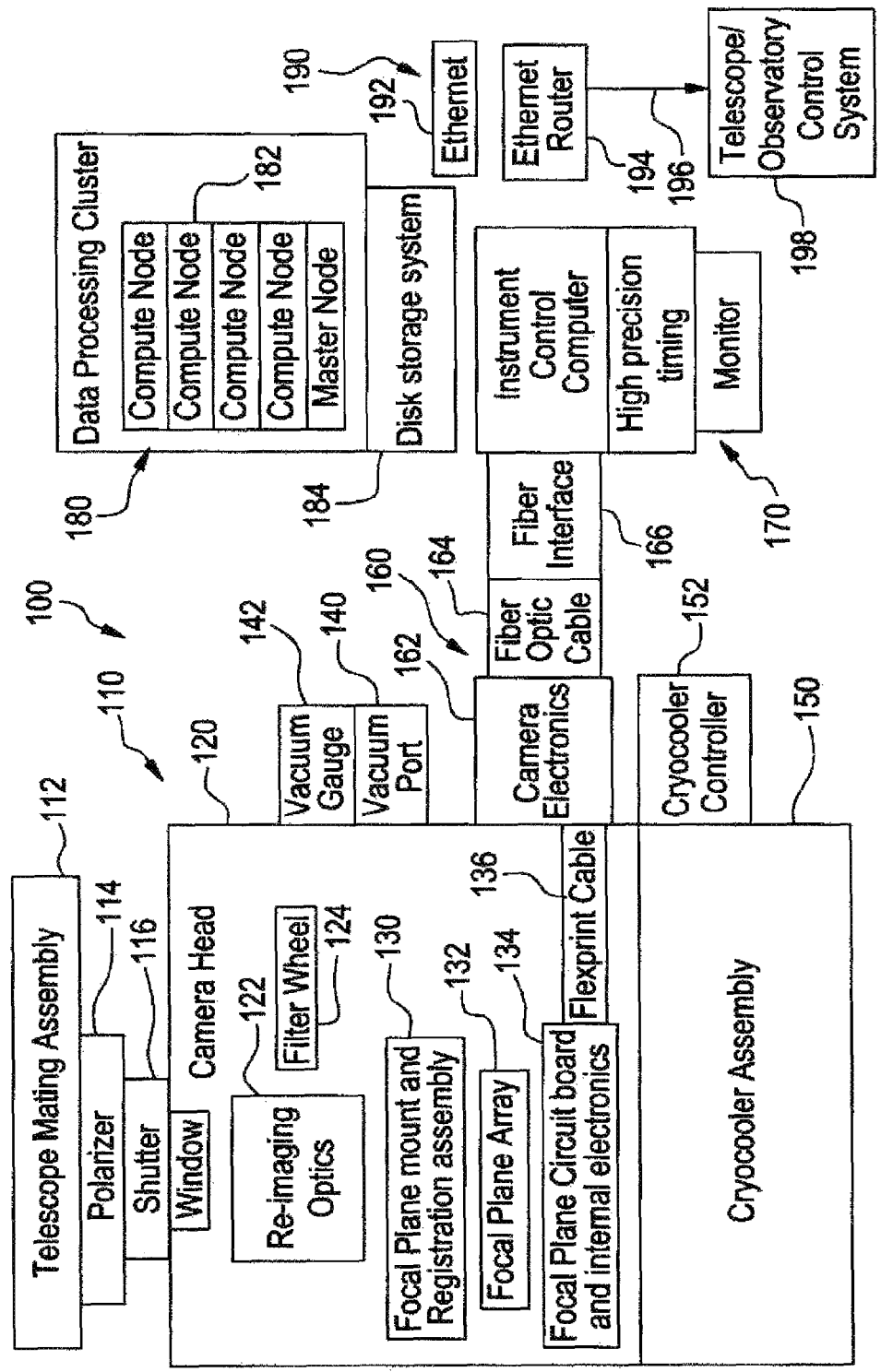
FIG. 11 schematically shows parts of a system for infrared daylight GEO satellite observance.

FIG. 11 schematically shows parts of a system for infrared daylight GEO satellite observance. The system 100 has a camera assembly 110, interconnections 160, a computer assembly 170, a data processing cluster 180 and communications 190. Camera assembly 110 has a telescope making assembly 112, a polarizer 114 and a shutter 116. A camera head 120 has re-imaging optics 122, a filter wheel 124, a focal plane mount and registration assembly 130, a focal plane array 132, a focal plane circuit board and internal electronics 134 and a flexprint cable 136.

A vacuum port 140 and a vacuum gauge 142 are connected to the camera head 120. A cryocooler assembly 150 is connected to the camera head. A cryocooler controller 152 is connected to the cryocooler 150.

Connections 160 include camera electronics 162, fiber optic cable 164 and a fiber interface 166.

A computer assembly 170 includes an instrument control computer 172, high precision timing 174 and a monitor 176.

Data processing cluster 180 includes compute nodes 182 and a disk storage system 184.

Communications 190 are provided by an internal ethernet 192. An ethernet router 194 provides a connection 196 to a telescope/observatory control system 198.

While the invention has been described with reference to specific embodiments, modifications and variations of the invention may be constructed without departing from the scope of the invention, which is defined in the following claims.

TABLE 1

Comparison of System Performance

| | Value Range | | | | Performance Improvement Range | | | Comment |
|---|---|---|---|---|---|---|---|---|
| | DAS (Maui) | Mojave (NM) | MATS | Oceanit Target System | | | | |
| 1 Aperture | 56 cm | 50 cm | 40 cm | 80 cm | 2.1 | 2.5 | 4 | SNR~aperture$^2$ |
| 2 F#, FOV | f/2.3 | f/8 | f/8.15 | f/11 | 4.8 | 1.4 | 1.4 | sky signal~1/F#$^2$, SNR~sqrt (sky signal) |
| 3 Pixel size | 30 | 30 | 30 | 20 | 1.25 | 1.25 | 1.25 | larger arrays have smaller pixles, SNR~sqrt(pix size) |
| 4 Detector noise performance | 70e- | 400e- | 700e- | 20e- | 1.1 | 2 | 3 | for BLIP sensing, camera noise is a contributing effect, not the only effect, so the advantage is less than the pure ratio of noises |
| Total | | | | | 14 | 9 | 20 | |
| Magnitudes | | | | | 2.8 | 2.3 | 3.3 | |

TABLE 2

Comparison of System Performance, Continued

| | Value Range | | | | Performance Improvement Range | | | Comment |
|---|---|---|---|---|---|---|---|---|
| | DAS (Maui) | Mojave (NM) | MATS | Oceanit Target System | | | | |
| 5 Filter | partial H | partial H | H | dual notch full band filters | 3 | 3 | 2.5 | Dual band + use of Kshort provides significant performance increase |
| 6 Integraton time | 0.016 | 0.016 | 0.06 | 1 | 8 | 8 | 4 | Longer integration improves SNR as the square root of time; however, for integration longer than ~2 seconds, sky variation may reduce the performance gain; 1 second is the system goal |
| Total | | | | | 24 | 24 | 10 | |
| Magnitudes | | | | | 3.5 | 3.5 | 2.5 | |

TABLE 3

Comparison of System Performance, Continued

| | | | | | | | | | Comment |
|---|---|---|---|---|---|---|---|---|---|
| 7 Frame Adding, threshold performance base frame x # added | 0.016 60 | 0.016 60 | 0.06 16 | 1 300 | 15 | 15 | 15 | Compare between current AFRL opinion that 1 second total equivalent integration time is achievable vs. 300 seconds total |
| Total | | | | | 15 | 15 | 15 | |
| Total magnitudes | | | | | 2.9 | 2.9 | 2.9 | |

TABLE 4

Comparison of Proposed Prototype System, Mojave and Final Target Systems

| | Value Range | | | Performance Comparison | | |
|---|---|---|---|---|---|---|
| | Mojave (NM) | Oceanit Prototype System | Oceanit Target System | Mojave to Prototype | Final to Prototype | Comment |
| 1 Aperture | 50 cm | 50 cm | 80 cm | 1 | 2.5 | SNR~aperture^2 |
| 2 F#, FOV | f/8 | f/8 | f/11 | 1 | 1.4 | sky signal - 1/F#^2, SNR~sqrt (sky signal) |
| 3 Pixel size | 30 | 20 | 20 | 1.25 | 1.25 | larger arrays have smaller pixles, SNR~ sqrt (pix size) |
| 4 Detector noise performance | 400e- | 20e- | 20e- | 2 | 2 | for BLIP sensing, camera noise is a contributing effect, not the only effect, so the advantage is less than the pure ratio of noises |
| 5 Filter | partial H | Kshort, H | dual notch H + Kshort | 1.3 | 3 | Dual band + use of Kshort provides significant performance increase |
| 6 Integraton time | 0.016 | 1 | 1 | 8 | 8 | Longer integration improves SNR as the square root of time; however, for integration longer than ~2 seconds, sky variation may reduce the performance gain; 1 second is the system goal |
| 7 Frame Adding, threshold performance base frame x # added | 0.016 60 | 1 30 | 1 300 | 5 | 15 | Compare between current AFRL opionion that 1 second total equivalent integration time is achievable vs. 30 seconds total |
| Total | | | | 130 | 3150 | |
| Total magnitudes | 7 | 12 | 15+ | 5.3 | 8.8 | |

We claim:

1. A method comprising detecting faint magnitude ~10 or greater (fainter) near IR reflections, providing interruptible and rapidly re-taskable ground-based intelligent network of autonomous globally distributed real-time interactive continuous 24/7 operating sensors, the providing the sensors comprising providing dedicated optical instruments having large focal ratios and large apertures, providing the instruments with a polarizer and a camera head, providing a window in the camera head, J, Kshort, H and K-band filters with a range of 1-3 μm wavelengths and detectors in a focal plane aligned with the window lenses and filters, the focal plane having 300 or more pixels, cryocooling the focal plane and camera optics, and repeatedly imaging a single area of sky during daytime, twilight, and nighttime with image integration times between 0.1 seconds and 180 seconds and coadding hundreds of image frames of the single area of sky and thereby removing star images and sky brightness changes, filtering wavelengths between 1 and 3 μm, reducing sky background, eliminating scattered sunlight longer than 1 μm and thermal wavelengths shorter than 3 μm, wherein the focal numbers greater than 5 reduce effect of sky brightness and thus lower noise, and wherein the coadding of the frames includes background subtraction in order to remove very bright sky backgrounds, wherein the detecting comprises daytime, twilight and nighttime detecting of deep space resident space-objects (RSOs).

2. The method of claim 1, further comprising reducing effect of sky brightness and lowering noise with focal ratios of the instruments, wherein the focal ratio has a focal number (F#) greater than or equal to 5.

3. The method of claim 1, further comprising improving target signal and increasing signal to noise ratio with apertures greater than or equal to 50 cm.

4. The method of claim 1, further comprising providing instrument clusters with no more than three lenses, and a dewar window.

5. The method of claim 1, further comprising providing the instruments as IR cameras with serviceable dewar windows and full control chip setup software.

6. The method of claim 5, further comprising integrating the IR reflections as information and then reading the information.

7. The method of claim 6, further comprising providing the IR cameras with detector chips that are removable and exchangeable.

8. The method of claim 5, further comprising providing cryogenic assemblies and providing changeable cold stops and near IR band filters in the cameras.

9. The method of claim 8, wherein the providing of filters comprises providing Kshort or K-band filters for daylight detecting.

10. The method of claim 9, further comprising reducing sky background by filtering out wavelengths between a scattered sunlight region below 2 μm and a thermal region above 2.5 μm.

11. The method of claim 8, wherein the providing of filters comprises providing combined Kshort band and H band filters for daylight detecting.

12. The method of claim 1, wherein the providing the detectors comprises providing InSb and MCT (HgCdTe) detectors and detecting H, K and Kshort bands.

13. The method of claim 1, further comprising providing background mitigation and long integration times.

14. The method of claim 13, further comprising providing frame coadding for the background mitigation.

15. The method of claim 1, further comprising providing cameras with cryogenic assemblies, providing Kshort or combined Kshort and H IR band filters in the cryogenic assemblies, providing integration times of 1 second, providing background mitigation by providing frame coadding of hundreds of image frames in the detectors, and obtaining performance levels in detecting during the day deep space resident space-objects and natural objects with orbital periods greater than 225 minutes, corresponding to what the Space Surveillance Network calls Deep Space Objects, and Low Earth Orbit and Medium Earth Orbit Objects.

16. The method of claim 15, further comprising using 300 or more small pixels as the image frames.

17. The method of claim 1, further comprising detecting LEO, MEO and GEO space objects at different longitudes or deep space orbits by dispersing the detectors around the world in longitudinal regions, directing the detectors at known satellites and other space objects and reporting status of such.

18. A system comprising an interruptible and rapidly re-taskable ground-based intelligent network of autonomous globally distributed real-time interactive continuous 24/7 operating sensors, each sensor comprising an instrument for faint magnitude ~10 or greater IR (infrared) detection from a resident deep space object (RSO) in deep space with orbital periods greater than 225 minutes, including geosynchronous Earth orbit and geosynchronous transfer orbit GEO/GTO during daytime, twilight and nighttime, the instrument being pointed at a known location of a RSO, the instrument comprising a camera head, the camera head comprising a window, lenses, filters and detectors in a focal plane aligned with the lenses and the filters, the focal plane having 300 or more pixels, a cryocooler, hundreds of image frames created by repeatedly imaging with the instrument a single area of sky during daytime, twilight, and nighttime and a processor configured for background subtraction and for coadding the hundreds of image frames of the single area of sky and thereby removing star images and sky brightness changes and detecting deep space objects.

19. The system of claim 18, wherein the filters comprise one or more band filters in the range from 1 to 3 microns.

20. The system of claim 19, wherein the filters are selected from the group consisting of J, H, Kshort, K, L band filters, and combinations thereof.

21. The system of claim 18, further comprising a polarizer.

22. A method comprising detecting and tracking faint magnitude ~10 or greater near IR reflections from satellites and resident space objects during daytime, twilight and nighttime, providing interruptible and rapidly re-taskable ground-based intelligent network of autonomous real-time interactive continuous 24/7 operating sensors repeatedly imaging with the instrument a single area of sky during daytime, twilight and nighttime, the providing the sensors comprising providing geographically spaced stations with dedicated optical instruments having large focal ratios of about f/5 or greater and large apertures of about 50 cm or greater, providing the instruments with cooled optics, and with near infrared J, H, Kshort, K and L band filters, and providing detectors having pixels less than 24 microns in length or width, providing the instruments with few light paths and few optical surfaces, providing cold traps and suppressing infrared background using a shift and stare technique of 0.1 second to 180 second integration in image frames combined with interactive background subtraction on a pixel by pixel basis and frame coadding, wherein 300 or more pixels are used as the image frames coadding images from hundreds of frames, thereby reducing sky background noise and allowing integration for one second or more and operating the instruments in an integrate and then read mode, wherein the detecting comprises daytime, twilight and nighttime detecting of low earth orbit, medium earth orbit and geosynchronous transfer orbit artificial objects, deep space resident space objects and geosynchronous orbit satellites and photovoltaic arrays.

23. A method comprising:
providing an interruptible and rapidly re-taskable ground-based intelligent network of autonomous globally distributed real-time interactive continuous 24/7 operating sensors,
providing each sensor comprising an instrument for faint magnitude ~10 or greater IR (infrared) detection from a resident deep space object (RSO) in deep space with orbital periods greater than 225 minutes, including geosynchronous Earth orbit and geosynchronous transfer orbit GEO/GTO during daytime, twilight and nighttime,
providing each instrument with a camera head comprising a window, lenses, filters and detectors in a focal plane aligned with the lenses and the filters,
having the focal plane with 300 or more pixels,
providing a cryocooler for cryocooling the focal plane and camera optics,
repeatedly imaging with the instrument a single area of sky during daytime, twilight, and nighttime,
creating hundreds of image frames with the repeatedly imaging,
processing and coadding the hundreds of image frames of the area of sky, removing star images and sky brightness changes, and
detecting deep space objects.

* * * * *